United States Patent [19]

Rubin

[11] Patent Number: 4,481,195
[45] Date of Patent: *Nov. 6, 1984

[54] METHOD FOR THE TREATMENT OF TUMORS WITH β-GLUCURONIDASE ACTIVITY DEPENDENT PHARMACEUTICALS

[75] Inventor: David Rubin, c/o Israel Medical Research Foundation, P.O. Box 3592, Jerusalem, Israel

[73] Assignees: Adolf Schwimmer, Savyon; Irwin S. Schwartz, Tel-Aviv; David Rubin, Jerusalem, all of Israel; Century Science Corp., Port Washington, N.Y.

[*] Notice: The portion of the term of this patent subsequent to Jul. 6, 1999 has been disclaimed.

[21] Appl. No.: 311,031

[22] Filed: Oct. 13, 1981

Related U.S. Application Data

[63] Continuation-in-part of Ser. No. 951,269, Oct. 13, 1978, and a continuation-in-part of Ser. No. 951,270, Oct. 13, 1978, Pat. No. 4,424,348, and a continuation-in-part of Ser. No. 11,619, Feb. 12, 1979, Pat. No. 3,630,146, and a continuation-in-part of Ser. No. 89,888, Oct. 31, 1979, Pat. No. 4,337,760.

[51] Int. Cl.$^3$ ..................... A61B 19/00; A61K 31/70
[52] U.S. Cl. .................................. 424/180; 128/1 R; 536/4.1; 536/17.9; 536/53
[58] Field of Search ..................... 424/180; 128/1 R

[56] References Cited

U.S. PATENT DOCUMENTS

| 2,985,664 | 5/1961 | Krebs et al. ............................ 536/4 |
| 3,959,253 | 5/1976 | Jones ..................................... 536/4 |
| 4,106,488 | 0/1978 | Gordon . |
| 4,181,132 | 0/1980 | Parks . |
| 4,327,074 | 4/1982 | Rubin ..................................... 424/9 |
| 4,337,760 | 0/1982 | Rubin . |

FOREIGN PATENT DOCUMENTS

| 2212014 | 10/1972 | Fed. Rep. of Germany . |
| 122386 | 10/1976 | German Democratic Rep. . |
| 788855 | 1/1958 | United Kingdom . |

OTHER PUBLICATIONS

Levi, L. et al., "Laetrile: A Study of its Physical and Biochemical Properties", Canad. Med. Ass. J., vol. 92, May 15, 1965, pp. 1057–1061.
Bicker, "Nature", vol. 252, Dec. 1974, pp. 726–727.
Fenselau et al., "Science" Nov. 1977, pp. 625–627.
Von Ardenne, M. et al, "Amplification of the Selective Tumor Acidification by Local Hyperthermia", Naturwissenschaften, 65, pp. 159–160 (1978).
Szasz, G. "Comparison Between p-Nitrophenyl Glucuronide and Phenolphthalein Glucuronide as Substrates in the Assay of β-Glucuronidase", Clinical Chemistry, No. 13, No. 9, pp. 752–759 (1967).
Nambara, T. et al, "New Synthesis of Phenolphthalein Glucuronide" Chem. Pharm. Bull., vol. 24, No. 11, pp. 2869–2870, 1976.
Von Ardenne, M. et al, "Anti-Cancer Agents with Activation in Strongly Hyperacidified Tumor Tissue: CMT-Selectines" Agressologie, 1976, 17, 5, 261–264.
Von Ardenne, M. et al, "Tumor pH and pH-dependent Increases in the Toxicity of Anti-Neoplastic Drugs", Pharmazie, 32 (2): 74–75, 1977.
Bicker, U., "Application of β-D-Glucuronides and Glucose Together Suggests a New Direction for Cancer Chemotherapy Nature, 252, Dec. 20–27, 1974 pp. 726–727.
Sweeney, M. J., et al, "Possible in Situ Activation of Mycophenolic Acid by β-Glucuronidase", Cancer Research, 31, 477–478, Apr. 1971.
Kaneko, M., et al, "Synthesis of D-Glucuronic Acid Derivatives of 5-Fluorouracil Having O-Glycosidic Linkage" Chem. Phar. Bull., 25 (9), 2458–2460 (1977).
Baba, T., et al, "5-Fluorouracil-O-β-D-Glucuronide as a Newly Synthesized Chemically Modified, Non--Toxic Anticancer Drug", Gann, 69, 283, 284, Apr. 1978.
Connors, T. A., "Cure of Mice Bearing Advanced Plasma Cell Tumors with Aniline Mustard: The Relationship Between Glucuronidase Activity and Tumor Sensitivity", Nature, Lond., 210, 866–867, 1966.
Bukhari, M. A., et al, "Aryl-2-halogenoalkylamines-XXVI-Glucuronic, Sulfuric and Phosphoric Esters of p-di-2-chloroethylaminophenol", Biochem. Pharm., 21, 963–967 (1972).
Ball, C. R., et al, "Enzyme-Activated Anti-Tumor Agents-Conjugates of p-hydroxyaniline Mustard as Substrates for Hydrolytic Enzymes", Biochem. Pharm., 23, 3171–3177, (1974).
Watabe, T. et al, "The Effect of Various Substituents on the Hydrolysis of Mono-substituted Phenol-β-D--Glucuronic Acids by β-Glucuronidase", Chem. Pharm. Bull. 18(2) 414–415 (1970).

(List continued on next page.)

Primary Examiner—Johnnie R. Brown
Attorney, Agent, or Firm—Browdy and Neimark

[57] ABSTRACT

Hyperacidified tumors having high β-glucuronidase activity can be treated with glucuronides with aglycones toxic to the tumor cells with great safety toward the rest of the body by first administering an alkalinizing agent in an amount sufficient to maintain the pH level of non-tumor tissues at approximately 7.4 during the glucuronide treatment. This will cause inactivation of β-glucuronidase activity in the rest of the body. When nitrile-containing aglycones are used sodium thiosulfate is also administered to avoid cyanide poisoning. A loading dose of glucuronide greater than 2 mMoles per kilogram body weight is first administered with additional administration of one third the initial dose each hour as long as β-glucuronidase activity remains at the tumor site. Bacterial cells having β-glucuronidase activity may also be diagnosed and treated in accordance with the present invention.

13 Claims, No Drawings

OTHER PUBLICATIONS

Wang, C-C et al, "Studies of Catalysis by β-Glucuronidase: The Effect of Structure on the Rate of Hydrolysis of Substituted Phenyl β-D-Glucopyranosiduronic Acids", *J. Biol. Chem.* 247, 9, 2650–2656 (1972).

Fenselau, C. "Mandelonitrile Beta-Glucuronidase: Synthesis and Characterization", *Science*, 198 (4317) 625–627, 1977.

Anghileri, L. J. et al, "Beta-Glucuronide Activity in Tumors: Accumulation of Radioiodinated Phenolphthalein", *Oncology* 25:19–32 (1971).

Mitchell, J. S. "Attempts to Develop Radioactive Drugs in the Treatment of Cancer", *Radiotracer Tech. Appl.* vol. 2, 1977, 1081–1110.

Gullino, T. M., et al, "Modifications of the Acid-Base Status of the Internal Milieu of Tumors", *Journal of the National Cancer Institute*, 34, 6, 857–869 (1965).

Bollenback, G. N., et al, "The Synthesis of Aryl-D-Glucopyranosiduronic Acids", *J. Am. Chem. Soc.*, 77, 3310–3315 (1955).

Levij, I. S., et al, "Inhibition by 2,4-Dinitrophenol of 9,10-Dimethyl-1,2-Benzanthracene Carcinogenesis in the Hamster Cheek Pouch", *Oncology*, 31, 334–337 (1975).

*Merck Index*, 9th edition, 7325 "Podophyllotoxin".

Schmidt, E. S., et al, "Laetrile Toxicity Studies in Dogs" *J.A.M.A.*, 239 (10) 943–947 (1978).

Lupo, M. et al, "Critical Review of Studies on Malignant Diseases", *Minerva Med.*, 67 (30) 1973–1981 (1976).

*Merck Index*, 9th edition "Laetrile".

Price, J. H. et al, "Laetrile-An Overview", *The Journal of School Health*, Sep. 1978, pp. 409–416.

*Federal Register*, vol. 42, #151, Friday, Aug. 5, 1977, pp. 39768+.

Trux, J. "New Controversy Surrounds Black Market Cancer Drug", *New Scientist*, pp. 132–133, Jul. 15, 1976.

Progress Reports No. 28–33, Merck Sharp and Dohme Research Laboratories, "Quarterly Project Report to Cancer Chemotherapy National Service Center, Contract PH-43-62-479", Jan. 1965 through Jun. 1966.

"The Magic Bullet that Missed", *Chemical and Engineering News*, vol. 31, 1540–1541, 1953.

"The treatment of Cancer with 'Laetriles': A Report by the Cancer Commission of the California Medical Association", *California Medicine*, vol. 78, No. 4, pp. 320–326, Apr. 1953.

METHOD FOR THE TREATMENT OF TUMORS WITH β-GLUCURONIDASE ACTIVITY DEPENDENT PHARMACEUTICALS

CROSS REFERENCE TO RELATED APPLICATIONS

The present application is a continuation-in-part of U.S. application Ser. No. 951,269, filed Oct. 13, 1978, U.S. application Ser. No. 951,270, filed Oct. 13, 1978, now U.S. Pat. No. 4,424,348, U.S. application Ser. No. 11,619, filed Feb. 12, 1979, now U.S. Pat. No. 3,630,146, and U.S. application Ser. No. 89,888, filed Oct. 31, 1979, now U.S. Pat. No. 4,337,760, the entire contents of each of which are hereby incorporated by reference.

FIELD OF THE INVENTION

The present invention relates to the treatment of tumors exhibiting B-glucuronidase activity by means of glucuronides having toxic aglycones and, more particularly, to an improvement of such process which eliminates damage to the kidneys. The toxic aglycones may incorporate a nitrile group.

BACKGROUND OF THE INVENTION

There have been many reports in the prior art relating to the general concept of providing direct transport of an agent which is toxic to tumor cells directly to tumors having β-glucuronidase activity by conjugating the agent with glucuronic acid. Among such reports are Von Ardenne, M. et al. Agressologie, 1976, 17, 5, 261-264; East German patent 122,386; German Offenlegungsschrift 22 12 014; Sweeney et al, Cancer Research, 31, 477-478, April 1971; Baba et al, Gann, 69, 283-284, 1978; and Ball, C. R., Biochem. Pharm., 23, 3171-3177 (1974).

The Von Ardenne reference suggests broadly many types of aglycones which may be conjugated to glucuronic acid and will be active at the tumor site. These include, broadly, alkylating groups, antimetabolites, cytotoxins, membrane-active (lytic) groups, glycolysis stimulators, respiration inhibitors, inorganic and organic acids and cell cycle stoppers. The East German patent also suggests many such combinations including 5-fluorouracil-glucuronide, methotrexate-glucuronide, 6-mercaptopurene-glucuronide, aniline mustard-glucuronide and many others. The Offenlegungsschrift also mentions a large number of glucuronides. The Sweeney article relates to the anti-tumor activity of mycophenolic acid-β-D-glucuronides, Baba relates to the anti-tumor activity of 5-fluorouracil-o-β-D-glucuronide, and Ball relates to the anti-tumor activity of p-hydroxyaniline mustard glucuronide.

It has also been reported that the selectivity of this transport mechanism can be improved by hyperacidification of the tumor cells. The Von Ardenne reference supra, as well as the East German patent, clearly recognize the importance and the feasibility of hyperacidification of the tumor cells when using the glucuronide mechanism. The Von Ardenne reference speaks of a method that yields a pH difference of at least 1 pH unit and may therefore by used as a basis for selectivity. It refers to reaching steady state conditions after hyperacidification in which the brain pH is 7.0 and the tumor tissue pH is approximately 5.5 to 6.0. Note also Von Ardenne, M. et al, Pharmazie, 32 (2): 74-75, 1977.

Bicker, U., Nature, 252, December 20-27, 1974, pp. 726-727, particularly notes that lysosomal enzyme β-glucuronidase has an optimum pH of 5.2 and that for anti-tumor activity of glucuronides, the pH must be lowered such as by the administration of glucose. Experiments are detailed which indicate that the hyperacidification by glucose is necessary in order to obtain significant deconjugation of glucuronides.

Even with hyperacidification of the tumor cells by known methods as, for example, glucose administration, however, there is still a problem in that other organs and tissues of the body which have a naturally occurring high β-glucuronidase activity, will also release the toxic aglycones and thereby cause damage to healthy tissues. This is most particularly a problem with regard to the kidney which normally has an acid pH environment.

It has been suggested in British patent 788,885 that mandelonitrile-β-D-glucuronic acid may be used in the treatment of malignant tumors as β-glucuronidase is prevalent in malignant tissues and will selectively attack mandelonitrile-β-D-glucuronic acid at the site of the malignant tumors to split off hydrogen cyanide. U.S. Pat. No. 2,985,664 is also related to mandelonitrile-β-D-glucuronic acid and a method of producing same. These compounds have been named Laetrile by the patentees of the above-mentioned patents.

SUMMARY OF THE INVENTION

Accordingly, it is an object of the present invention to overcome the deficiencies of the prior art.

It is another object of the present invention to provide for the improved treatment of malignant tumors.

It is a further object of the present invention to provide an improved process for the treatment of malignant tumors having high β-glucuronidase activity.

It is still another object of the present invention to provide such an improved process which is selectively toxic to tumor cells, but does not harm healthy tissue.

It is yet another object of the present invention to provide such an improved process in which the tumor cells are selectively treated with nitrile-containing compounds with concurrent therapy to avoid the possibility of cyanide poisoning in the rest of the body.

It is another object of the present invention to provide such an improved process in which the dosing is optimized and the side effects due to the presence of necrotic products are minimized.

It is still another object of the present invention to provide a process for the treatment of bacterial injections when the bacteria exhibit β-glucuronidase activity.

These and other objects of the present invention will be better understood from a reading of the following summary and the detailed description of the present invention.

It has now been found that the selectivity of glucuronide compounds toward tumors can be greatly increased and the possible deconjugation of the toxic aglycones in normal parts of the body can be greatly minimized by administering to the patient, prior to or simultaneously with administration of the glucuronide, an alkalinizing agent which will maintain the pH of the rest of the body at a pH of about 7.4. It is known that at a pH of 7.4 and above β-glucuronidase activity is substantially nil. Thus, the administration of alkalinizing agents such as bicarbonates or other basic salts will substantially decrease and eliminate β-glucuronidase activity which naturally occurs in certain healthy tissues such as the kidneys, spleen, and liver. Such an administration of alkalinizing agent will not diminish the acidity of the tumor cells themselves, however, in view of the naturally low pH of the tumor cells, the mechanism of prior hyperacidification, and the lack of substantial blood perfusion through the tumor areas, as well as other possible mechanisms. It has been suggested in the literature, in fact, that bicarbonate will actually increase the acidity of the cancer cells. Gullino, P. M., et al, J.N.C.I., 34, 6, 857–869 (1965).

Since the β-glucuronidase activity of the tumor cells will be enhanced by acidification, and the β-glucuronidase activity of the rest of the body, particularly of the kidneys, will be substantially eliminated by alkalinization, the toxic aglycones will only be released at the tumor site itself due to deconjugation of the glucuronides by the action of β-glucuronidase. Without the alkalinization step, substantial amounts of toxic materials may be released, for example, in the kidneys, and the toxic aglycones so released may cause substantial damage to these organs. Thus, only through the use of the present invention can glucuronides of compounds toxic to tumor cells be used clinically with a great degree of safety. The greater the toxicity of the aglycones, the more important is the alkalinization step.

In order to further eliminate the possibility of release of toxic aglycone in the entero-hepatic system, a further precaution which may be taken is to sterilize the intestines by means of neomycin in order to eliminate any β-glucuronidase-producing bacterial flora in the intestine. This may be done by administering an antibiotic, such as neomycin, orally three times a day before glucuronide administration.

Other steps for increasing β-glucuronidase activity at the tumor cells may also be undertaken. One method of doing this is to elevate the temperature of the toxic cells at the time of treatment. This may be done by elevating the temperature of the entire body such as by use of a pyrogenic drug or by elevating the temperature soley in the area of the toxic cells, such as by microwave radiation or electrical current. Raising of the temperature increases β-glucuronidase activity thereby increasing the efficiency of the deconjugation of the glucuronides. It is known that an elevation of temperature of 3° C. increases β-glucuronidase activity by 50%.

Known pyrogenic drugs include etiocholanolone, progesterone, dinitrophenol, dinitrocresol, etc. Both dinitrophenol and dinitrocresol are also cytotoxic, as will be discussed hereinbelow. Therefore the use of these compounds are preferred, especially when administered as the glucuronide. This gives the result that when the glucuronide is deconjugated at the tumor site the aglycone will act not only to denature the cytoplasmic protein but also to raise the temperature directly in the region of the tumor cells thus greatly increasing the efficiency of further deconjugation.

Local hyperthermia in the region of suspected tumor cells is preferred to general hyperthermia because general hyperthermia will also increase the β-glucuronidase activity in healthy cells. However, because of the alkalinization step this is not a major problem. If the hyperthermia is local, then this provides an additional degree of certainty that the glucuronides will only become deconjugated at the tumor site. The application of microwave treatment directed at the suspected tumor site is one way to achieve local hyperthermia. Due to the different electrical resistence of tumor cells, another method of achieving some degree of local hyperthermia is by administering a low electrical current through the body.

A further manner of increasing β-glucurondase activity selectively at tumor cells is by administration of estrogen to female patients or testosterone to male patients. It has been reported that these compounds induce β-glucuronidase activity in trophoblastic cells. Certain tumor cells are known to be trophoblastic; this method would thus be particularly useful for those cells. The alkalinization step would prevent damage to healthy trophoblastic cells.

Another feature of the present invention resides in an additional safety feature by which the healthy tissues of the body are protected against possible release of hydrogen cyanide from nitrile-containing aglycones. This feature is preferably in addition to the feature disclosed hereinabove with respect to pH adjustment. Even with such protection against deconjugation of the glucuronide at areas of the body other than tumors, concern has been expressed about possible cyanide poisoning when using nitrile-containing glucuronides. For example, in Schmidt, E. S., et al. J.A.M.A. 239 (10):943–7, 6 March 78, it was predicted that there will be an increased incidence of cyanide poisoning in man as Laetrile (amygdalin) becomes more readily available. It is not known whether it is the entire nitrile-containing aglycone, mandelonitrile, which exerts the toxic effect on the tumor cells, or whether it is the hydrogen cyanide which is released upon the decomposition of mandelonitrile. It is theorized, however, that it is the entire nitrile-containing aglycone which exerts the toxic effect on the tumor cells. Therefore, it is important to protect the rest of the body against possible release of hydrogen cyanide from nitrile-containing aglycones. This is accomplished in accordance with the present invention by the concurrent administration of sodium thiosulfate when glucuronides of nitrile-containing aglycones are used. It is well known that sodium thiosulfate is an antidote for cyanide poisoning. Sodium thiosulfate in the presence of the enzyme rhodanase converts hydrogen cyanide to sodium thiocyanate.

It is believed that the concurrent administration of sodium-thiosulfate will not affect the toxicity of the aglycone at the cancer site for two reasons. First, even in the presence of rhodanase, sodium thiosulfate will not affect the mandelonitrile molecule itself. Therefore, if it is the entire mandelonitrile molecule which is toxic to the cancer cells, then the presence of sodium thiosulfate will not affect this toxicity. Furthermore, even if it is the hydrogen cyanide which is toxic to the cancer cells when released at the site of the cancer cells, it has been suggested in the literature that cancer cells do not contain rhodanase. See Lupo, M. et al, "Critical Review of Studies on Malignant Diseases," Minerva Med. 67 (30) 1973–1981, 1976. Therefore, the concurrent administration of sodium thiosulfate will protect normal cells against cyanide poisoning but will not affect the attack of the cyanide on the tumor cells.

In view of the relative lack of toxicity of glucuronide compounds, and in view of the mechanism of the present invention by which the toxic aglycone is released only at the tumor site, and further in view of the protection of the present invention against possible hydrogen cyanide release at other parts of the body, it is entirely possible to use glucuronides of other toxic nitrile-containing aglycones in the process of the present invention. One such compound is methacrylonitrile β-D-glucuronic acid.

The process of the present invention may not only be used against tumors but also against bacteria of the type having high β-glucuronidase activity. It is known, for example, that streptococcus, staphylococcus and *E. coli* bacteria have β-glucuronidase activity. Therefore, if the glucuronides come into contact with these bacteria, they will become deconjugated and the cytotoxic aglycones will be toxic to the bacteria.

It has been reported that the optimum pH of bacterial β-glucuronidase is higher than the optimum pH of the β-glucuronidase of normal healthy internal organs, such as liver, spleen, kidney, etc. Therefore, upon alkalinization of the body in accordance with the method discussed hereinabove, the β-glucuronidase activity of the organs will be substantially eliminated, while that of the bacteria, although alkalinized, will still be present. The administered glucuronide will then only be deconjugated to its active form at the site of the infection. Since tumor cells are not being treated for this utility, no hyperacidification step is necessary.

The preferred dosages for administration of glucuronides in accordance with the present invention, whether for the treatment of tumors having β-glucuronidase activity, or bacteria having β-glucuronidase activity, includes an initial loading dose of at least 2 mMol of glucuronides per kg of body weight of the patient. This amount of glucuronide should be administered during 5–10 minutes in 100 cc of 5% dextrose solution. This loading dose is based on the fact that the enzymatic reaction of β-glucuronidase does not take place when the concentration of the substrate is less than 10 mMols. It is known that the extra-cellular component of the human body is about 20% by weight of the body weight. Accordingly, in order to obtain a concentration of at least 10 mMols, it should be considered that the glucuronide being administered will be diluted in fluids amounting to 20% of the body weight. Thus, 20% of 10 mMols × the body weight in kgs is equal to 2 mMols per kg of body weight.

It has been noted that the blood level of glucuronide is reduced by ⅓ in the first hour after administration. Accordingly, every hour during the course of administration, ⅓ of the loading dose should be administered in a 10% glucose solution in order to keep the proper concentration of the substrate throughout the entire treatment. Treatment should be continued as long as β-glucuronidase remains at the tumor site.

The initial degradation of the glucuronide to release the toxic aglycone at the cancer site takes place due to the excess β-glucuronidase at the cancer site, as well as the membrane linked β-glucuronidase at the cancer site. After this initial reaction, the intoxicated cells, and some other cells of the tumor, will start the necrotic process which then releases lysosomal β-glucuronidase. At this time, a second course of glucuronide treatment in accordance with the present invention should be repeated, usually two to five days after the first course.

Further in accordance with the present invention, in order to help the body eliminate the toxic necrotic products which are the breakdown products of the cancer cells, an anti-ammonia intoxication procedure should be carried on during the treatment. This procedure should include treatment and diet equivalent to that administered to patients suffering from cirrhosis of the liver, for example, 500 mg Neomycin orally three times a day in addition to low protein diet and acidophilus tablets.

DETAILED DESCRIPTION OF PREFERRED EMBODIMENTS

EXAMPLE I

Method of Administration of Glucuronide Therapy

After it has been determined that the patient has a tumor with β-glucuronidase activity by means of diagnostic methods discussed in each of said parent applications, which methods are hereby incorporated by reference, the first step of the treatment is to give the patient a course of antibiotics in order to sterilize any β-glucuronidase-producing bacteria in the intestinal flora. Preferably an antibiotic, such as neomycin, is administered three times a day, beginning at least a day prior to administration of the glucuronide and continued through the glucuronide treatment. After the intestines have been sterilized, a does of glucose as, for example, 100 g of honey, glucose or other sugar. Approximately one hour later an intravenous drip is begun of a solution in distilled water containing approximately 10% glucose and 60 milli-equivalents of sodium bicarbonate. Approximately 1 liter is administered, assuming no contraindications, and the pH of the urine is checked to determine that it has reached a pH of approximately 7.4. This will establish that the system has become alkalinized and it is now safe to administer the glucuronide. 2 mMols of glucuronide per kilogram of body weight of the patient is then administered in 100 cc of 5% dextrose solution during a 5 to 10 minute period. This glucuronide administration is repeated every hour with ⅓ of this initial loading dose, i.e., ⅔ mMol of glucuronide per kilogram of body weight. This is repeated every hour for a 24 hour period or as long as β-glucuronidase exists in the tumor. The β-glucuronidase activity of the tumor may be monitored in order to determine when the course of treatment should be halted.

After this initial treatment period, the β-glucuronidase level of the patient is monitored. When an abrupt increase of β-glucuronidase activity is noted, usually 2–5 days after the first course of treatment, the initial course of treatment is repeated.

Throughout the treatment the patient is maintained on a low protein diet and acidophilus tablets are administered.

When a glucuronide of a nitrile-containing cytotoxic aglycone is being used, immediately before, during, or after administration of the glucuronide, 50 cc of a 25% solution of sodium thiosulfate is administered, preferably intravenously by slow drip. The sodium thiosulfate is preferably included in the glucuronide solution. However, it may also be continued afterward for a greater margin of safety.

If there are contraindications for the administration of bicarbonate, then antacid may be orally administered. The important criterion is that the pH of the urine become approximately 7.4 and remain so during treatment.

The hyperacidification of the tumor cells is caused by a hyperglycemic condition in the patient. Therefore any hyperglycemic agent may be used as the hyperacidification agent, as for example, fructose, galactose, lactose or glucagon. Furthermore, it should be understood that this hyperglycemic condition may be effected in any known manner. For example, if the patient is diabetic then the condition can be brought about by decreasing the insulin administration.

Any agent which will raise the pH of the urine to approximately 7.4 can be used as the alkalinizing agent, including sodium or potassium bicarbonate or citrate, or other basic salts or antacids. While it is preferred that these be administered intravenously, they may be administered orally.

When the term "approximately 7.4" is used in the present specification and claims, with respect to the pH level to be maintained in the rest of the body, it should be understood that a pH level slightly above or below 7.4 may be used, although not preferred. As the pH decreases from 7.4 the $\beta$-glucuronidase activity increases (until the optimal pH is reached). Furthermore, below pH 7.0 the rest of the body will not be alkaline but will be acid. Above 7.4 the danger of alkalosis increases without any substantial further decrease in $\beta$-glucuronidase activity. A pH level of 7.4 is preferred as this is physiological pH and cannot be harmful to the body, and it is known that the $\beta$-glucuronidase activity in healthy organs is substantially nil at this pH level.

Besides intravenous administration, the glucuronides may be administered by any means of parenteral administration. However, the glucuronides should not be administered orally as it is known that $\beta$-glucuronidase is present in the digestive tract. The sodium thiosulfate, however, can be administered orally if a proper enteric coating is provided to avoid release in the stomach.

The maximum amount to be administered to any given patient must be determined empirically and will differ depending on the condition of the patient. Of course, the maximum safe toxicity dosage as determined in routine animal toxicity tests should never be exceeded.

It is clear that any tumor cells having $\beta$-glucuronidase activity may be treatable in accordance with the present invention with the remaining organs of the body being protected by the alkalinization step. Tumors which are known to have $\beta$-glucuronidase activity include solid breast tumors and their metastases, bronchogenic carcinoma and its metastases, and lymphomas. It is also known that neoplasms that do not have high $\beta$-glucuronidase activity, and therefore cannot be treated in accordance with the present invention, include leukemia. It must be understood, however, that this list is not meant to be complete, and that the prior art is aware of many other tumors that have $\beta$-glucuronidase activity. However, whether or not the art is presently aware that any given tumor has $\beta$-glucuronidase activity, this can be determined by any of the various methods of diagnosis discussed in the present specification and if it is determined that the tumor does have $\beta$-glucuronidase activity, the therapeutic treatment of the present invention can be effectively used.

When it is desired to induce hyperthermia to increase $\beta$-glucuronidase activity, a method should be selected by which the temperature is raised as much as possible without risking damage to healthy portions of the body, such as the eyes. An increase of about 2° C. for whole body hyperthermia and as much as 4.5° C. for local hyperthermia is preferred. The hyperthermia should be timed to last about an hour at the time of greatest glucuramide concentration at the tumor site. For example, when local microwave treatment is selected, it should begin about one half hour after commencement of the intravenous glucuronimide drip and be continued for about an hour. The proper dosage of known pyrogens to achieve the desired degree of hyperthermia would be known to those skilled in the art or could be easily empirically determined. A dosage of about 30 mg/day for dinitraphenol, for example, would be apt.

When estrogen or testosterone are to be administered, a dosage of 5-15 mg/body wt/day would provide the desired inducement of $\beta$-glucuronidase activity.

EXAMPLE II

Method of Anti-Bacterial Administration

Glucuronide administration may be used in the treatment of bacterial infections if the bacteria involved are known to have $\beta$-glucuronidase activity. Examples of such bacteria are streptococci, staphylococci, and *E. coli*. The method of treatment of such bacterial infections will be similar to the method set forth in Example I except that no hyperacidification will be necessary. This is so because bacterial $\beta$-glucuronidase is active at higher pH levels than $\beta$-glucuronidase of normal healthy internal organs. Furthermore, such a hyperacidification step would not affect the pH of the bacteria as its mechanism is specific to tumor cells. Intestinal sterilization is also not absolutely necessary, particularly if the aglycone is itself an antibiotic.

The first step in antibacterial administration is an intravenous drip of distilled water and 60 milliequivalents sodium bicarbonate. Approximately one liter is administered and the pH of the urine is checked to determine that it has reached a pH of approximately 7.4. At least 2 mMols of glucuronide per kg of body weight is then administered in 100 cc of 5% dextrose solution over a 5-10 minute period.

The alkalinizing agent may also be orally administered and any agent may be used that will alkalinize the body to an extent such that the pH of the urine becomes approximately 7.4. The glucuronide should not be administered orally but it may be administered by any means of parenteral administration.

Certain known anti-bacterial drugs having adverse side-effects may also be administered as glucuronides in accordance with the method of the present invention in order to reduce or eliminate these adverse effects. For example, chloroamphenicol is known to have a bone marrow depression effect which will not take place if the glucuronide is used. Neomycin is a known antibacterial which cannot be administered parenterally because of its toxicity. However, it can be administered for the treatment of infections of bacteria having high $\beta$-glucuronidase activity if first conjugated to glucuronic acid.

Besides the cytotoxic glucuronide compounds which are usable in the anti-tumor processes discussed hereinabove, any known conjugatable antibiotic may be conjugated with glucuronic acid for use against $\beta$-glucuronidase containing infections. This has the advantage of greatly diminishing the amount of free antibiotic circulating in the blood stream. The only antibiotic which is released will be released at the site of the infection. Therefore much smaller dosages may be given. Accordingly, the glucuronides of the present invention can serve as an internally administered local antibiotic. Such a method of administration is particularly useful for the treatment of infections of the bile duct or other locations in which it has been particularly difficult in the past to obtain a sufficient concentration of antibiotic. Because of the known $\beta$-glucuronidase activity in the digestion tract, no glucuronide should be administered orally, although any mode of parenteral administration is permissible.

If the antibiotic aglycone is known not to have any effect on the kidneys, then the alkalinization step can be eliminated. Many antibiotics, however, are known to be nephrotoxic to some extent and thus the alkalinization step is important to protect the kidneys.

It will be obvious to those skilled in the art that various changes may be made without departing from the scope of the invention and the invention is not to be considered limited to what is described in the specification.

What is claimed is:

1. In a process of selectively delivering the aglycone of a glucuronide compound to tumor cells having higher $\beta$-glucuronidase activity than that of the surrounding tissues by hyperacidifying the tumor cells and then administering to the patient a glucuronide compound, the aglycone of which is to be delivered to the tumor cells, whereby the $\beta$-glucuronidase activity of the hyperacidified tumor cells causes deconjugation of the glucuronide compound at the site of the tumor cells and release of the aglycone thereat, the improvement wherein the tumor selectivity of the process is improved and the risk of deconjugtion of the glucuronide compound at the site of non-tumor tissues is diminished, comprising:

administering to the patient an alkalinizing agent in an amount sufficient to maintain the pH level of the non-tumor tissues of the patient at approximately 7.4 during the glucuronide treatment, and the improvement further comprising administering said glucuronide in an initial dosage of at least 2 mMols per kg of body weight but not exceeding the maximum safe toxicity dosage.

2. A process in accordance with claim 1, wherein said compound is one in which the aglycone is toxic to tumor cells and exerts a higher toxic effect in an acid environment than in an alkaline environment or is water-soluble in an alkaline environment and water-insoluble or only poorly water-soluble in an acid environment.

3. A process in accordance with claim 2, wherein said glucuronide compound is selected from the group consisting of 2,4-dinitrophenol-$\beta$-D-glucuronic acid; 4-chloro-m-cresol-$\beta$-D-glucuronic acid; 4,6-dinitro-o-cresol-$\beta$-D-glucuronic acid; 4-chloro-3,5-xylanol-$\beta$-D-glucuronic acid; chlorothymol-$\beta$-D-glucuronic acid; 5-chloro-7-iodo-8-quinolinol-$\beta$-D-glucuronic acid; podophyllotoxin-$\beta$-D-glucuronic acid; 2-phenyl-6-chlorophenol-$\beta$-D-glucuronic acid; p-iodophenol $\beta$-D-glucuronic acid; and phenylsulfazole-$\beta$-D-glucuronic acid.

4. A process in accordance with claim 1, wherein said step of hyperacidifying the tumor cells comprises administering a hyperglycaemic agent in an amount sufficient to hyperacidify the tumor cells.

5. a process in accordance with claim 1, wherein said alkalinizing agent is administered orally or intravenously.

6. A process in accordance with claim 1, wherein said alkalinizing agent is administered prior to administration of said glucuronide compound, said glucuronide compound being administered after the pH of the urine of the patient is determined to be approximately 7.4 and wherein administration of said alkalinizing agent continues during administration of said glucuronide compound.

7. A process in accordance with the claim 1 wherein the aglycone of said glucuranide compound is nitrile containing and further including the step of administering to the patient an amount of sodium thiosulfate sufficient to serve as antidote for cyanide poisoning.

8. A process in accordance with claim 1, further including the step of inducing hyperthermia at least at the site of the tumor being treated to an extent sufficient to substantially increase $\beta$-glucuronidase activity at the site without substantially affecting the overall health of the patient at least at the time of maximum glucuronide concentration at the tumor.

9. A process in accordance with claim 8, wherein said hyperthermia is induced locally at the tumor by administration of the glucuronide of a pyrogen, by microwave treatment or by passage of electrical current through the body.

10. A process in accordance with claim 1 further including the step of administering estrogen or testosterone substantially simultaneously with the administration of said glucuronide.

11. A process in accordance with claim 1 wherein said initial dosage of glucuronidase is followed by administration of a dosage thereof equalling about one third of said initial dosage each hour following said initial dosage for a period of about 24 hours.

12. A process in accordance with claims 1 or 11 wherein said glucuronide administration is repeated 2–5 days after said first administration, when an abrupt increase of $\beta$-glucuronidase activity is noted in the patient.

13. A process in accordance with claim 1 wherein throughout said treatment the patient is also treated to alleviate or avoid ammonia intoxication.

* * * * *